US007163611B2

(12) United States Patent
Völkel et al.

(10) Patent No.: US 7,163,611 B2
(45) Date of Patent: Jan. 16, 2007

(54) CONCENTRATION AND FOCUSING OF BIO-AGENTS AND MICRON-SIZED PARTICLES USING TRAVELING WAVE GRIDS

(75) Inventors: Armin R. Völkel, Mountain View, CA (US); Meng H. Lean, Santa Clara, CA (US); Huangpin Ben Hsieh, Mountain View, CA (US); Jurgen Daniel, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 270 days.

(21) Appl. No.: 10/727,289

(22) Filed: Dec. 3, 2003

(65) Prior Publication Data

US 2005/0123992 A1 Jun. 9, 2005

(51) Int. Cl.
*B01D 57/02* (2006.01)

(52) U.S. Cl. ...................................... 204/547; 204/643

(58) Field of Classification Search ................ 204/450, 204/456, 457, 461, 466, 547, 549, 606, 643, 204/645

See application file for complete search history.

(56) References Cited

U.S. PATENT DOCUMENTS

| | | | | |
|---|---|---|---|---|
| 4,473,452 A | | 9/1984 | Cantor et al. | |
| 4,647,179 A | | 3/1987 | Schmidlin | |
| 4,737,251 A | | 4/1988 | Carle et al. | |
| 5,208,458 A | | 5/1993 | Busch et al. | |
| 5,534,121 A | | 7/1996 | Merrick et al. | |
| 5,569,367 A | * | 10/1996 | Betts et al. | 204/547 |
| 5,626,734 A | * | 5/1997 | Docoslis et al. | 204/547 |
| 5,653,859 A | | 8/1997 | Parton et al. | |
| 5,837,116 A | | 11/1998 | Harrington et al. | |
| 6,149,789 A | * | 11/2000 | Benecke et al. | 204/547 |
| 6,272,296 B1 | | 8/2001 | Gartstein | |
| 6,296,752 B1 | * | 10/2001 | McBride et al. | 204/547 |
| 6,358,752 B1 | | 3/2002 | Durst et al. | |
| 6,398,933 B1 | | 6/2002 | Scott | |
| 6,499,831 B1 | | 12/2002 | Schmidlin | |

(Continued)

FOREIGN PATENT DOCUMENTS

EP 0 558 233 A1 * 2/1993

(Continued)

OTHER PUBLICATIONS

Scott Rudge et al., Electroseparations (Electrophoresis), *Encyclopedia of Chemical Technology*, 4th Edition, vol. 9, pp. 356-376.

(Continued)

*Primary Examiner*—Nam Nguyen
*Assistant Examiner*—Anthony Fick
(74) *Attorney, Agent, or Firm*—Fay, Sharpe, Fagan, Minnich & McKee, LLP

(57) ABSTRACT

Several traveling wave grid systems are disclosed that may be used to concentrate and form highly localized regions of bio-agents or other charged species. In addition, specific detection systems are described that enable currently available detectors and sensors, including those to be developed in the future, to be used for measuring the presence and concentration of certain bio-agents or charged particles, which otherwise are present at concentrations too low to readily detect or measure.

11 Claims, 10 Drawing Sheets

U.S. PATENT DOCUMENTS

| | | | | |
|---|---|---|---|---|
| 6,596,143 | B1 * | 7/2003 | Wang et al. | 204/547 |
| 6,949,355 | B1 * | 9/2005 | Yamanishi et al. | 435/34 |
| 2001/0023825 | A1 | 9/2001 | Frumin et al. | |
| 2002/0144895 | A1 | 10/2002 | Stern et al. | |
| 2003/0015467 | A1 | 1/2003 | Johnston et al. | |
| 2003/0027135 | A1 | 2/2003 | Ecker et al. | |
| 2003/0034290 | A1 | 2/2003 | Tochikubo et al. | |

FOREIGN PATENT DOCUMENTS

| | | |
|---|---|---|
| WO | WO 99/36357 | 7/1999 |
| WO | WO 00/73780 | 12/2000 |

OTHER PUBLICATIONS

O'Hara et al., *Ratcheting Electrophoresis Microchip* (*REM*) *for Programmable Transport and Separation of Macromolecules*, MEMS, Nov. 11-16, 2001, pp. 619-628, vol. 3, ASME, USA.

Dunphyet al., *Rapid Separation and Manipulation of DNA by a Ratcheting Electrophoresis Microchip* (*REM*), Nov. 17-22, 2002, pp. 419-423, ASME, USA.

Proteome Systems, Products, Website, *ElectrophorestIQ*$^3$ , 2002 at http://www.proteomesystems.com/product/product.asp-?ProductID=43 and http://www.proteomesystems.com/product/profile.asp?DocumentID=662.

ISC Buyers' Guide, Website, *Electrophoresis, 2D Gel*, 2002, at http://www.iscpubs.com/bg/us/prod/prod1991.html.

EMBL's Proteomics Visitor Facility, Website, 2D Gel Equipment, *Protean 2D Cells from Bio-Rad, 2001, at http://.mann.embl-heidelberg.de/Visitor*_Facility/PageLinks/Instrumentation/GelchamberMain.html, and *Protean IEF Cell from Bio-Rad*, at http://www.mann.embl-heidelberg.de/Visitor_Facility/PageLinks/Instrumentation/ECellMain.html.

James R. Jefferies,, *2D Gel Electrophoresis for Proteomics Tutorial*, pp. 1-24 at http://www.aber.ac.uk/parasitolgy/Proteome/Tut_2D.html (last tutorial update: Jan. 7, 2003).

The Scripps Research Institute, Website, *Proteomics Module*, 2003, pp. 1-3 at http://core-eye.scripps.edu/proteomics.htm.

2D Protocols, Website, *Analysis of Proteins Using Small Format 2D Gel Electrophoresis*, 2000, pp. 1-5, at http://www.abdn.ac.uk/~mmb023/protocol.htm.

Biowire.com, Website, *The Nucleus*, 2000-2002, pp. 1-4, at http://www.biowire.com/nucleus/nucleus_1_3.jsp.

Bio-Rad Laboratories, Website, *Electrophoresis*, 2003, at http:www.bio-rad.com/B2B/BioRad/produict/br_category.jsp.

British Berkefeld, *James Filter*, http://www.jamesfilter.com/, Jun. 23, 2003.

Filtros Ltd., *Filtros*, http//www.filtrosltd.com/, Jun. 23, 2003.

REI, http://www.rei.com/, Jun. 23, 2003.

* cited by examiner

CONCENTRATION AND FOCUSING OF BIO-AGENTS AND MICRON-SIZED PARTICLES USING TRAVELING WAVE GRIDS

TECHNICAL FIELD

The present subject matter relates to the field of electrophoretic separation of bio-agents and particles, and more particularly, to their focusing into regions of relatively high concentrations. The present subject matter also relates to analytical systems and methods employed after concentrating the bio-agents or particles by use of an electric field.

BACKGROUND

Electrophoresis is a separation technique most often applied to the analysis of biological or other polymeric samples. It has frequent application to analysis of proteins and DNA fragment mixtures. The high resolution of electrophoresis has made it a key tool in the advancement of biotechnology. Variations of this methodology are used for DNA sequencing, isolating active biological factors associated with diseases such as cystic fibrosis, sickle-cell anemia, myelomas, and leukemia, and establishing immunological reactions between samples on the basis of individual compounds. Electrophoresis is an extremely effective analytical tool because it does not affect a molecule's structure, and it is highly sensitive to small differences in molecular charge and mass.

Particles can be manipulated by subjecting them to traveling electric fields. Such traveling fields are produced by applying appropriate voltages to microelectrode arrays of suitable design. Traveling electric fields are generated by applying voltages of suitable frequency and phases to the electrodes.

This technique of using traveling electric fields relates to an important method for separation and sorting of large particles and cells referred to as dielectrophoresis. Dielectrophoresis is defined as the movement of a polarisable particle in a non-uniform electric field. Essentially, the force arises from the interaction of the field non-uniformity with a field induced charge redistribution in the separated particle.

Particles are manipulated using non uniform electric fields generated by various configurations of electrodes and electrode arrays. As a general biotechnological tool, dielectrophoresis is extremely powerful. From a measurement of the rate of movement of a particle the dielectric properties of the particle can be determined. More significantly, particles can be manipulated and positioned at will without physical contact, leading to new methods for separation technology.

A powerful extension of dielectrophoresis separation is traveling wave dielectrophoresis (TWD) in which variable electric fields are generated in a system of electrodes by applying time varying electric potential to consecutive electrodes. Such a method of Traveling Wave Field Migration was described by Parton et al. in U.S. Pat. No. 5,653,859, herein incorporated by reference. Although satisfactory, a need for improved strategies and methodologies remains. In addition, dielectrophoresis requires higher voltage (~100 V), higher frequencies (~10 MHZ), and finer electrode pitch (<10 um).

A microfluidic device for electrophoretic separation of biomolecules such as DNA and protein was described by Dunphy et al. in "Rapid Separation and Manipulation of DNA by a Ratcheting Electrophoresis Microchip (REM)," Proceedings of IMECE2002, Nov. 17–22, 2002, New Orleans, La., No. IMECE2002-33564, herein incorporated by reference. The device utilizes thousands of electrodes along the length of a microchannel. An electrical potential is applied across the electrodes and selectively varied to separate molecules within the microchannel into two groups using a ratcheting mechanism. This mechanism does not employ traveling waves. Although directed to the separation of biomolecules, this strategy is based upon micro device technology and is not readily compatible with conventional laboratory equipment. Accordingly, a need exists for a device and technique for utilizing electrostatic traveling waves for selectively concentrating bio-agents and particles, and particularly, for subsequent analysis.

In the bio-sciences the detection of miniscule concentrations of bio-agents, e.g. molecules, complexes, spores, cells, etc., is of high importance. Examples include the detection of low-abundance proteins for understanding cell function or the detection of harmful bio-agents, e.g. toxins, viruses, microbes, spores, parasites, etc., that can pose a risk even at very low concentrations. However, most detection methods only work above the concentration of material that is available in the native probe. Therefore, sample preparations that allow the extraction of bio-agents from a large volume and subsequent concentration into a smaller volume (the detection area) are crucial to the success of this task. Therefore, there is a need for a method to concentrate bio-agents (or any other charged molecule or small particle) suspended in a liquid into a smaller volume.

Detection of miniscule concentrations of bio-agents (molecules, spores, low-abundance proteins, cells, bacteria, etc.) is important for both science and health/safety. Most detection systems require concentrations higher than those occurring in the environment. Therefore, sample preparations are needed that can extract bio-agents from a large volume and concentrate them into a smaller volume.

BRIEF DESCRIPTION OF THE DISCOVERY

In a first aspect, a system for selectively concentrating an agent within a fluid medium is provided. The system comprises a first traveling wave grid having a first substrate, a first collection of closely spaced and parallel electrically conductive electrodes extending across the first substrate, and a first collection of buses providing electrical communication with the first collection of electrodes. The system also comprises a second traveling wave grid having a second substrate, a second collection of closely spaced and parallel electrically conductive electrodes extending across the second substrate, and a second collection of buses providing electrical communication with the second collection of electrodes. The system also comprises an effective amount of a fluid medium adapted to accommodate the agent undergoing migration therein. The fluid medium is in contact with at least a portion of the first collection of electrodes and at least a portion of the second collection of electrodes. The system also comprises at least one voltage controller providing a multi-phase electrical control signal to the first collection of buses, the first collection of electrodes, the second collection of buses, and the second collection of electrodes. The voltage controller is configured to apply the control signal to the first traveling wave grid and the second traveling wave grid such that the agent migrates through the fluid medium at least partially across the first traveling wave grid in a direction generally perpendicular to the direction of the first collection of electrodes. And, the agent further migrates through the fluid medium at least partially across the second traveling wave grid in a direction generally perpendicular to the direction of the second collection of electrodes.

In another aspect, a method for concentrating an agent dispersed within a fluid medium by use of a system of traveling wave grids is provided. The system includes a first traveling wave grid having a substrate, a collection of electrodes, and buses providing electrical communication with the electrodes. The system also includes a second traveling wave grid having a substrate, a collection of electrodes, and buses providing electrical communication with the electrodes of the second grid. The system also includes a voltage controller providing a control signal to the electrodes of the first and second traveling wave grids. The method comprises a step of providing the fluid medium containing the agent in proximity to the first and second traveling wave grids. The method also includes a step of sequentially applying the control signal to the collection of electrodes of the first traveling wave grid to induce movement of that agent in the fluid medium to form a first region in the medium of high concentration of agent. The method also includes a step of sequentially applying the control signal to the collection of electrodes of the second traveling wave grid to induce further movement of the agent in the fluid medium to thereby form a second region in the medium of high concentration of agent.

In another aspect, a selectively addressable traveling wave grid system is provided. The system comprises a point electrode grid including a substrate and a collection of individually addressable, electrically conductive point electrodes disposed on the substrate. The system also comprises a voltage controller providing a multi-phase control signal. And, the system includes a collection of electrical contacts providing electrical communication between the point electrode grid and the voltage controller. Each of the point electrodes may be individually selected to receive the control signal.

In a further aspect, a method for concentrating an agent dispersed within a fluid medium by use of a selectively addressable traveling wave grid system is provided. The system includes a point electrode grid having a substrate and a collection of individually addressable, electrically conductive point electrodes disposed on the substrate. The system also includes a voltage controller providing a multi-phase control signal. The system further includes a collection of electrical contacts providing electrical communication between the point electrode grid and the voltage controller. The method comprises an operation of providing the fluid medium containing the agent in proximity to the point electrode grid. The method comprises another operation of applying the control signal to a first portion of the collection of point electrodes that are disposed in a first row on the substrate. The method includes another step of applying the control signal to a second portion of the collection of point electrodes that are disposed in a second row on the substrate. A region is formed in the medium having a relatively high concentration of agent.

In still another aspect, a system for detecting agents in a flowing fluid medium is provided. The system comprises a filter element adapted to collect agents dispersed in a fluid medium having a size greater than the pass through size limit of the filter element. The system also comprises a traveling wave grid having a collection of electrically conductive electrodes disposed on the filter element. The system further comprises a voltage controller adapted to provide a multi-phase control signal to the collection of electrodes. And, the system further comprises a detector adapted to detect agents in the fluid medium. The detector is disposed in proximity to a region of the traveling wave grid.

In still another aspect, a method for detecting agents in a flowing fluid medium is provided. A system is used having a filter element adapted to collect agents dispersed in a fluid medium having a size greater than the pass through size limit of the filter element. The system also includes a traveling wave grid having a collection of electrically conductive electrodes disposed on the filter element. The system further includes a voltage controller adapted to provide a multi-phase control signal to the collection of electrodes. And, the system includes a detector adapted to detect agents in the fluid medium. The detector is disposed proximate to a region of the traveling wave grid. The method comprises a step of positioning the filter element and the traveling wave grid of the system in the flowing fluid medium such that the traveling wave grid is upstream of the filter element. The method includes another operation of collecting agents having a size greater than the pass through size limit of the filter element along the filter element. The method includes another operation of activating the traveling wave grid by selectively applying the control signal from the voltage controller to portions of the collection of electrodes whereby the agents collected on the filter element are moved to the detector. The method further comprises a step of detecting agents moved from the filter element by the traveling wave grid and the controller.

Still further advantages and benefits of the present discovery will become apparent to those of ordinary skill in the art upon reading and understanding the following detailed description of the preferred embodiments.

BRIEF DESCRIPTION OF THE DRAWINGS

The present subject matter may take form in various components and arrangements of components, and in various steps and arrangements of steps. The drawings are only for purposes of illustrating preferred embodiments and are not to be construed as limiting the subject matter.

DETAILED DESCRIPTION OF THE PREFERRED EMBODIMENTS

Figure 1A:
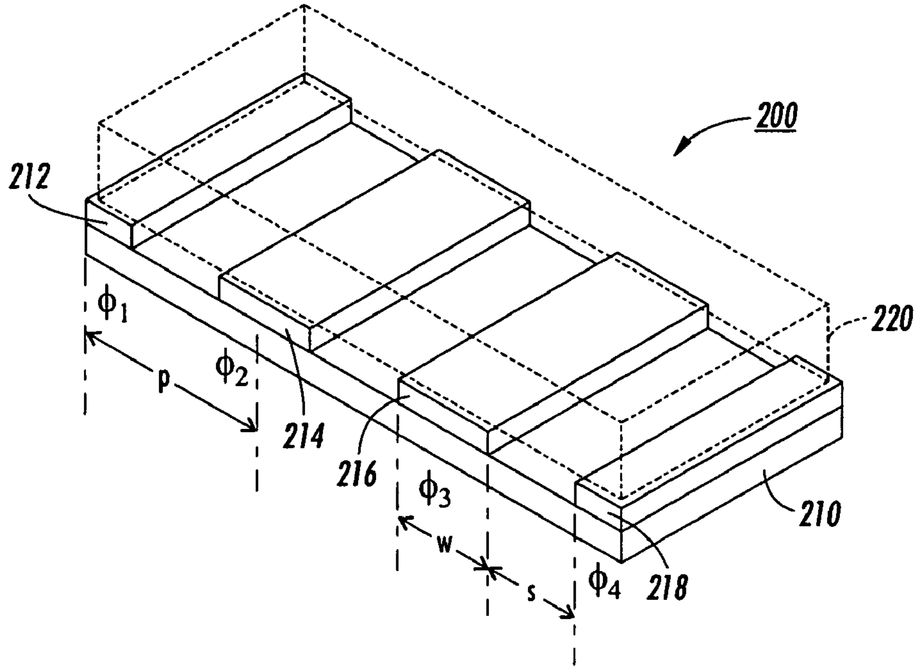
FIG. 1A is a schematic illustration of a preferred single sided traveling wave grid configuration.
Figure 1B:
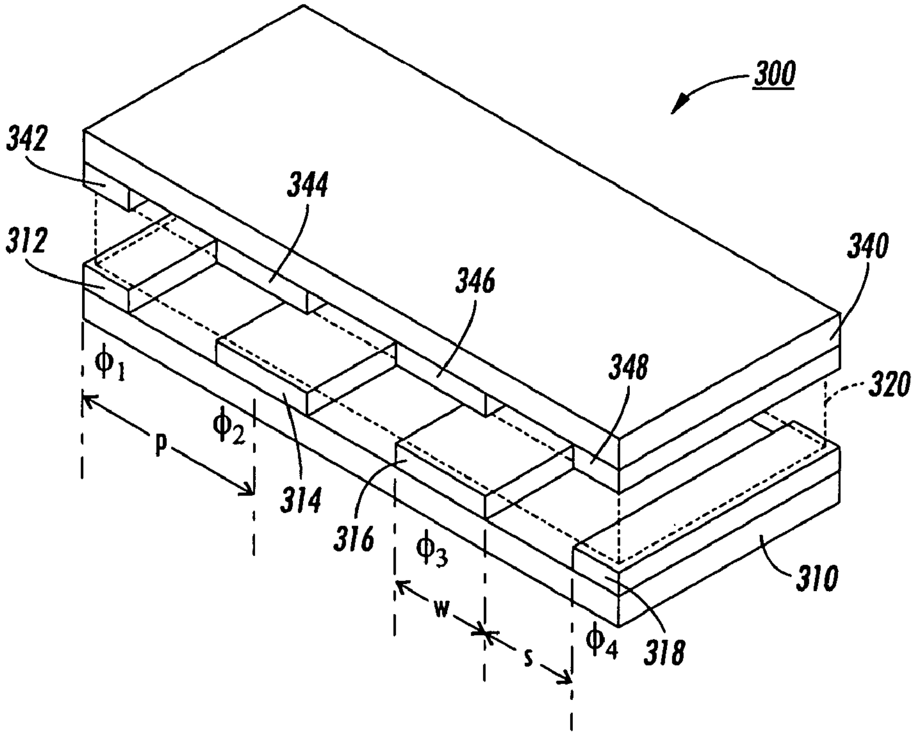
FIG. 1B is a schematic illustration of a preferred double sided traveling wave grid configuration.

FIGS. 1A and 1B are schematic illustrations of preferred embodiment single and double sided traveling wave grid assemblies. The assemblies include an effective amount of a liquid or gel disposed in intimate relation thereto. Specifically, FIG. 1A is a single sided grid assembly 200 comprising a plate 210, a plurality of parallel and closely spaced electrodes 212, 214, 216, and 218, and an effective amount of a liquid 220 in electrical communication with the electrodes. Most preferably, the electrodes are formed from platinum or alloys thereof. It is also preferred to deposit a thin layer of titanium on the plate, which is preferably glass, to promote adhesion between the electrodes and plate. As described herein, it is preferred to utilize a four (4) phase electrical signal in conjunction with the preferred embodiment systems, assemblies, and grids noted herein. Accordingly, it is preferred that a first electrode such as electrode 212 be utilized for a first phase $\phi 1$ of the electrical signal. Similarly, it is preferred that a second electrode immediately adjacent to the first, such as electrode 214, be utilized for a second phase $\phi 2$ of the electrical signal. And, it is preferred that a third electrode immediately adjacent to the second electrode, such as electrode 216, be utilized for a third phase $\phi 3$ of the electrical signal. Moreover, it is preferred that a fourth electrode immediately adjacent to the third electrode, such as electrode 218, be utilized for a fourth phase $\phi 4$ of the electrical signal. As described in greater detail herein, the distance between the centers of adjacent electrodes is referred to as pitch, and denoted as "p." The width of an electrode is denoted as "w." And the distance between facing sidewalls or edges of adjacent electrodes is "s."

FIG. 1B is a schematic illustration of a preferred double sided traveling wave grid assembly 300 comprising a first plate 310; a first plurality of parallel and closely spaced electrodes 312, 314, 316, and 318; a second plate 340; a second plurality of parallel and closely spaced electrodes 342, 344, 346, and 348; and an effective amount of a liquid or gel 320 in electrical communication with the first and second plurality of electrodes.

Figure 2:
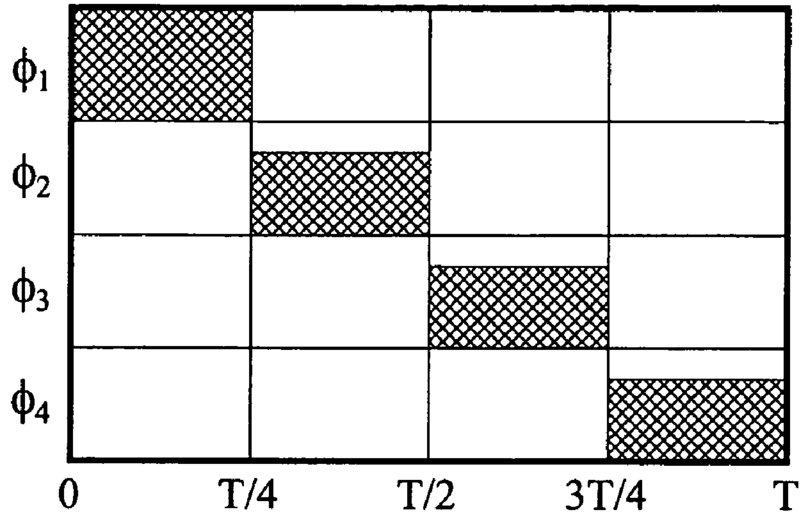
FIG. 2 is a representative four phase traveling wave voltage pattern employed in the preferred systems and traveling wave grids.
Figure 3:
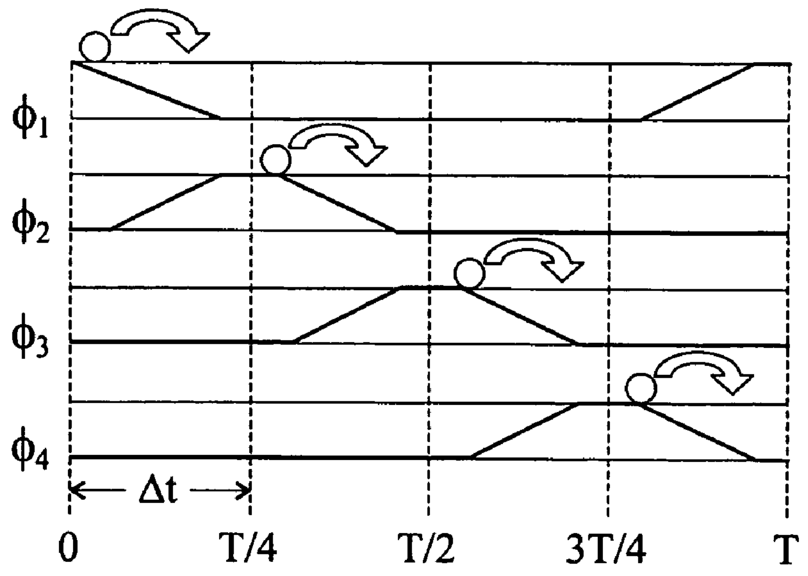
FIG. 3 is a schematic illustration of biomolecule transport from one electrode to another.

FIG. 2 is a representative four phase voltage pattern or waveform used in the preferred embodiment systems and traveling wave grids of the present discovery. Specifically, FIG. 2 depicts the four phase voltage waveform with 90 degree separation between phases. Each waveform occurring in each phase is a square wave pulse. Each pulse is sequentially applied to an adjacent electrode. Thus, a first pulse in phase $\phi 1$, is applied to a first electrode for a desired time period, such as T/4. Upon completion of that first pulse, such as at time T/4, a second pulse in phase $\phi 2$ is applied to a second electrode, preferably immediately adjacent to the first electrode. Upon completion of that second pulse, such as at time T/2, a third pulse in phase $\phi 3$ is applied to a third electrode, preferably immediately adjacent to the second electrode. Upon completion of that third pulse, such as at time 3T/4, a fourth pulse in phase $\phi 4$ is applied to a fourth electrode, preferably immediately adjacent to the third electrode. This sequential and ordered array of voltage pulsing results in bio-agents or particles dispersed in the liquid to "hop" from the vicinity of one electrode to another. The synchronous mode of propagation is depicted in FIG. 3 and may be described as a "hopping" mode where the bio-agent or particles hop from electrode to electrode in the direction of the pulse train. The transit time to migrate across the dielectric space is then given by:

$$t_{transit}=s/\mu E,$$

where pitch is given by p=w+s, and w and s are the electrode width and dielectric space, respectively. Electric field and mobility are given by E and $\mu$, respectively. The period for one cycle through the four phases is $4*t_{transit}$, so that the maximum sweep frequency is:

$$f<\mu E/4s.$$

For sustained transport, the bio-agent or particle has to have sufficient speed ($\mu$E) and time (ttransit) to traverse the distance of the dielectric space, s. This equation implies that for sustained transport, there is a critical frequency for bio-agents or particles of a certain mobility. Therefore, by starting with the highest operational frequency, one can progressively scan downwards in frequency until the bio-agent or particle of the right mobility starts to move. This means that for certain bio-agents, the fastest (and lowest molecular weight) bio-agents, i.e. biomolecules, may be separated out from the sample one at a time.

In another preferred embodiment, the present discovery provides an electrophoretic system having a distributed multi-segmented traveling wave grid. The system includes a layer of a liquid or gel, a multi-segmented system of traveling wave grids, and a voltage controller in electrical communication with the grids. Each of the grid segments includes a plurality of closely spaced parallel electrodes that are in contact with the liquid. The voltage controller is adapted to provide one or more selectable multi-phase electrical signals to one or more of the grid segments. In a particularly preferred embodiment, the voltage controller provides a first multi-phase electrical signal to at least one of the grid segments and a second multi-phase electrical signal to all or only some of the grid segments. In still other preferred aspects, the system may comprise two, three, or more voltage controllers that may be configured to provide one or more particular multi-phase electrical signals to one or more grid segments of the traveling wave grid.

Figure 4:
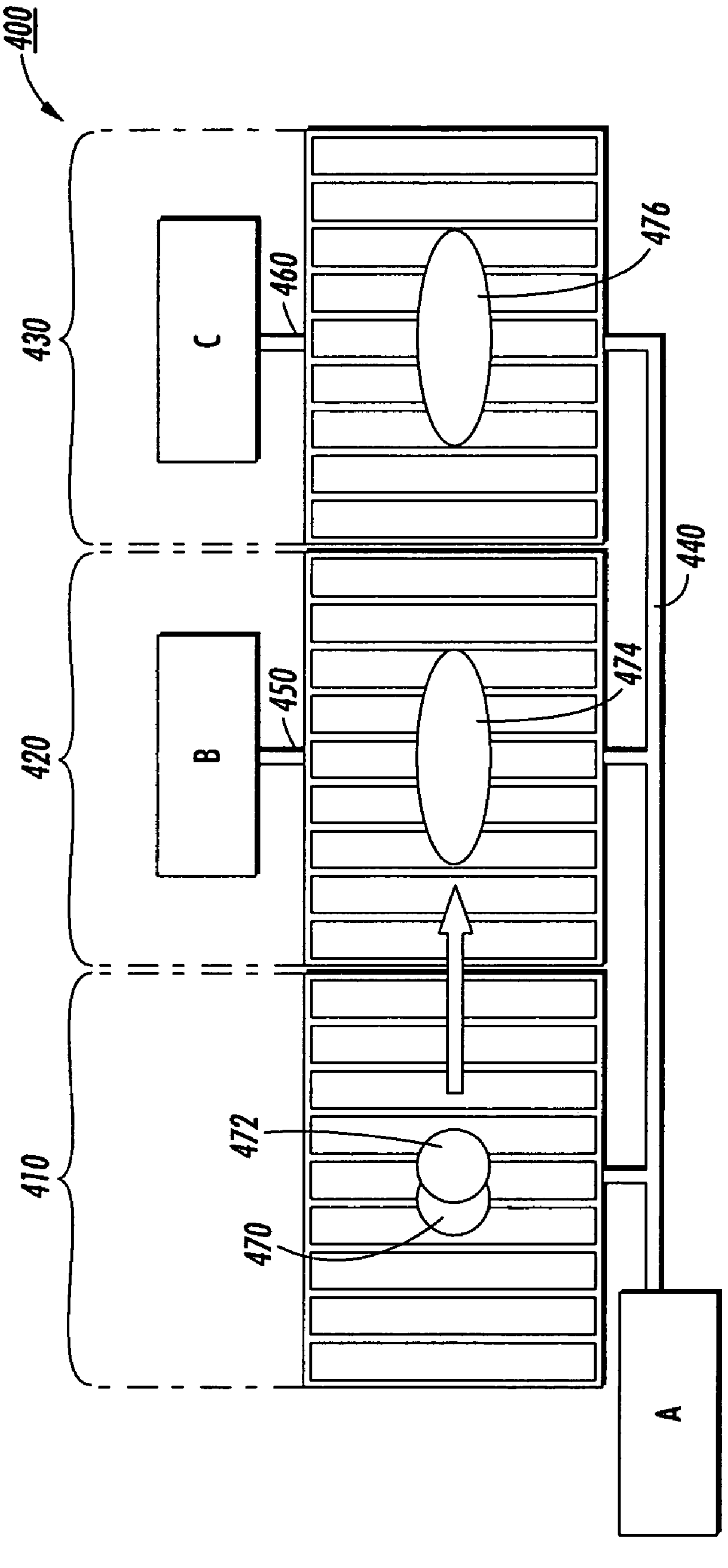
FIG. 4 is a schematic illustration of a preferred embodiment electrophoretic system utilizing distributed, reconfigurable, and reprogrammable traveling wave grids.

The present work provides significant opportunity for innovation in the design of specific systems of traveling wave grids to focus, separate, and concentrate bio-agents and particles. One preferred strategy is to fabricate the smallest pitch possible for the traveling wave grids for maximum flexibility in reconfiguring the grids for specific applications. FIG. 4 is a schematic illustration of a preferred embodiment electrophoretic system 400 utilizing multiple distributed, reconfigurable, and reprogrammable traveling wave grids. Specifically, FIG. 4 shows a preferred multi-segmented traveling wave grid system. The preferred multi-segmented traveling wave grid system includes a first grid segment 410, a second grid segment 420, and a third grid segment 430. As will be appreciated, each segment includes a plurality of parallel and closely spaced electrodes. Two contiguous pads on respective sides together offer connection to the four phase circuit through one or more buses 440, 450, and 460. The system 400 preferably further includes one or more programmable voltage controllers such as controllers A, B, and C depicted in FIG. 4. As will be appreciated, the controllers are in electrical communication with the traveling wave grid (or segments thereof) through the noted buses.

In utilizing the preferred embodiment system 400, one particularly preferred strategy involves moving bio-agents or particles of interest onto individual local traveling wave grid segments using controller A where they are then available for subsequent processing using controllers B, C and so forth. Each controller may be a separate PIC implementation or a single PIC with multiple pre-programmed instructions. For example, in operation, the preferred embodiment system 400 of FIG. 4 may be utilized to separate a sample of various biomolecules as follows. A sample 470 is deposited onto the grid segment 410. The sample migrates to region 472 and continues to migrate onto adjacent grid segment 420. Operation of system 400 continues until a region 474 of biomolecules forms within grid 420. Depending upon the biomolecules and grid parameters, the biomolecules constituting region 474 may further migrate to adjacent grid segment 430, and form a region 476 of biomolecules. Generally, this strategy utilizes an initial separation using a first controller and secondary refinements or further separation using other controllers and segments of grids. Secondary refinements include further concentrating of migrated biomolecules and focusing of bands or patches.

In still another preferred embodiment, the present discovery provides a process for separating various biomolecules from a sample. The process utilizes an electrophoretic system comprising a layer of a liquid or gel suitable for electrophoresis, the layer being disposed between two co-planar substrates. The system also includes a traveling wave grid which includes at least a first grid segment and a second grid segment. The system additionally includes a voltage controller in selective communication with the first grid segment and the second grid segment. The process comprises a first step of depositing the sample containing the biomolecules on the layer of the liquid. Next, a first multi-phase electrical signal, such as a four phase electrical signal, is applied to one or both of the first and second grid segments. This causes at least a portion of the biomolecules in the sample to migrate in the liquid. A second multi-phase electrical signal is applied to one or both of the first and second grid segments to further cause either the same portion of biomolecules to further migrate in the liquid or another portion of biomolecules in the sample to migrate in the liquid. By selectively applying appropriate multi-phase electrical signals to one or both of the grid segments, the sample can be selectively analyzed or separated.

If the system utilizes multiple voltage controllers, the process can further apply one or more multi-phase electrical signals generated by those additional controllers to various grid segments as desired. Additionally, each of the various voltage controllers used in this system may be configured to provide varying or changing multi-phase electrical signals. Changes in these signals may include changes in voltage levels, frequency, or other electrical parameters. Additionally, the present discovery includes processes in which the interface between a voltage controller and one or more of the traveling grids is changed. For instance, a multi-phase electrical signal maybe applied to a particular array of electrodes in a grid. After a desired stage of the separation process has been reached, the electrodes to which the multi-phase electrical signal is applied are changed. This strategy may be used to selectively analyze and separate a wide array of biomolecules in a sample.

The present subject matter also provides a method for concentrating particles suspended in a liquid, by employing multiple traveling wave grids with or without bias fields to concentrate these particles from two or three dimensions into a single spot or highly localized region. Traveling wave grids concentrate suspended charged particles into bands parallel to the grid electrodes. Often, particularly high operating efficiencies are realized when operating the grids such that the band of suspended particles is located a distance above the grid that is approximately equal to the electrode spacing of the grid. Depending upon the height above the grid, a small to moderate bias field can push charged particles (either positive or negative) closer to the traveling wave surface. Combining two grids that concentrate particles in perpendicular directions, the systems of the present discovery focus the particles into single spots or regions of high concentration. To counteract diffusion, a high viscosity medium, such as a gel may be utilized within which the particles are retained.

Figure 5A:
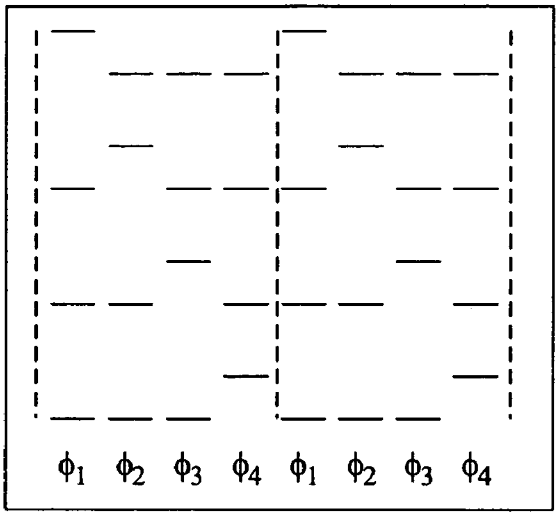
FIG. 5A illustrates a spatial voltage waveform applied to a traveling wave grid over two time periods.
Figure 5B:
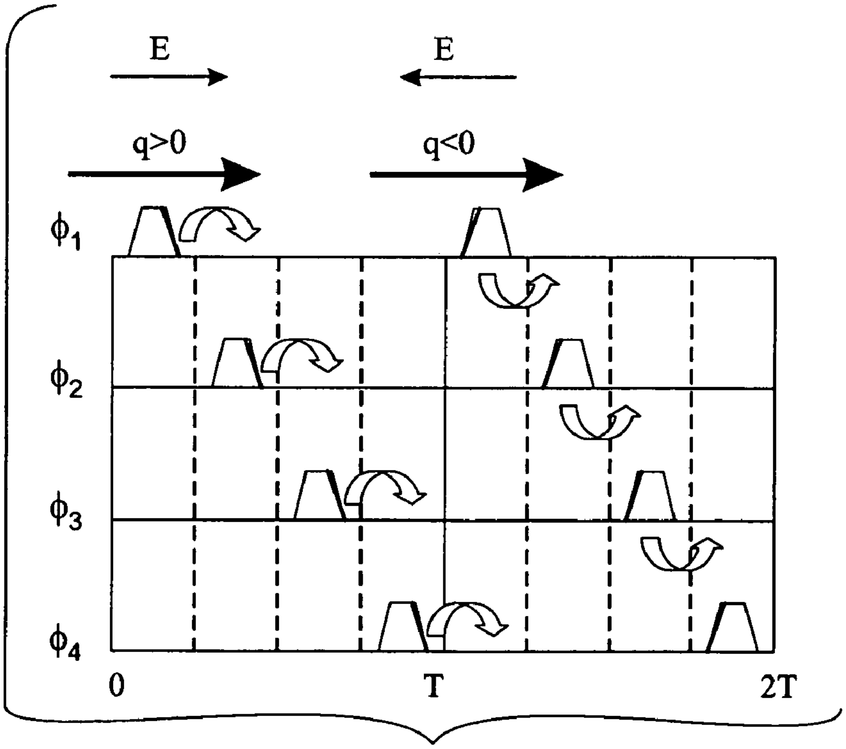
FIG. 5B illustrates a temporal voltage waveform over two time periods and the corresponding transport of a bio-agent or particle.

A traveling wave grid can concentrate particles, i.e. charged particles, that are suspended in a liquid above or proximate the grid into narrow bands parallel to the grid electrodes. FIG. 5A illustrates a schematic of a traveling grid wave. Specifically, FIG. 5A depicts a spatial voltage waveform applied to the grid over two time periods (2T), and applied through a four phase signal. FIG. 5B shows the corresponding voltage pattern that is applied to the two sets of four contiguous electrodes. Depending on the particle size and concentration, the gel can be replaced by a lower viscosity medium, such as certain liquids.

Figure 6A:
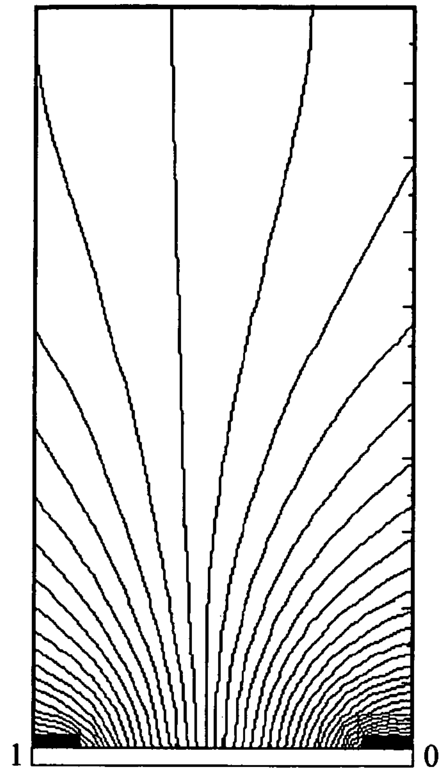
FIG. 6A is a schematic diagram illustrating an electric field resulting from two adjacent electrodes in a traveling wave grid.
Figure 6B:
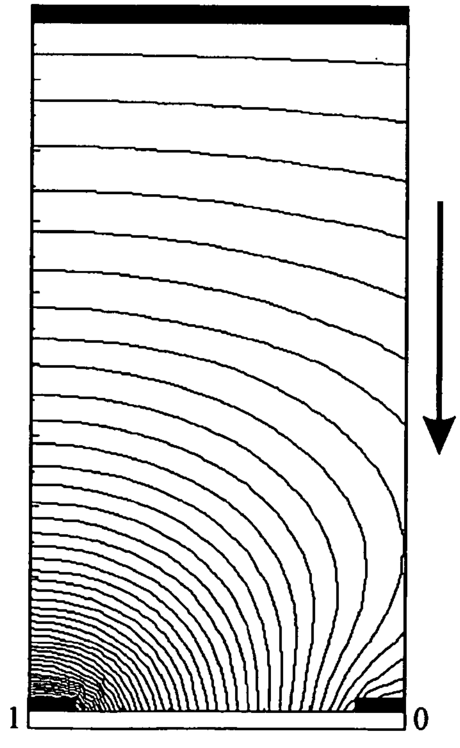
FIG. 6B is a schematic diagram illustrating the effect upon the electric field shown in FIG. 6A by positioning a bias field in proximity to the electrodes.

Charged particles hop from electrode to electrode with the traveling wave. Because the wave has a positive as well as a negative potential gradient, charges of both polarity both move with the direction of the wave, but are phase shifted by the width of the pulse. This is shown in FIGS. 5A and 5B. Particles can only move with the traveling wave, if their mobility is high enough to keep up with the speed of the wave. Also, since the electric field strength decreases with increasing distance from the traveling wave grid, efficient transport (hopping mode) is only possible for particles sufficiently close to the grid. However, numerical simulations have shown that a moderate bias field (on the order of 1 V/m) is sufficient to keep the particles close to the traveling wave grid. In addition, this small bias field also helps to increase the field component parallel to the grid. This is shown in FIGS. 6A and 6B. Specifically, FIG. 6A illustrates an electric field resulting from application of an electrical signal to two adjacent electrodes of a traveling wave grid as previously described herein. The electrodes of FIG. 6A are characterized by a pitch p of 40 μm and a spacing s of 30 μm. FIG. 6B illustrates the effect upon the electric field by positioning a bias field in close proximity to the electrodes. The bias field results from applying a −0.025V potential to a planar conductor. The planar conductor is denoted in FIG. 6B as the thick dark region at the top of that figure.

Depending on the medium above the grid and the desired application, charged particles can be either accumulated in a single line at one end of the grid, or in individual lines parallel to the grid depending on specific parameters of the particles and the type of waveform applied to the traveling wave grid.

By combining two traveling wave grids such that the electrodes of the two grids extend in a perpendicular fashion to each other, the particles can be further concentrated into a single region. To achieve a higher particle concentration, the focusing is preferably performed in a high-viscosity medium, e.g. a gel.

A system for selectively concentrating an agent within a fluid medium is provided as follows. The system comprises a first traveling wave grid having a substrate, a collection of closely spaced and parallel electrically conductive electrodes extending across the substrate, and a collection of buses providing electrical communication with the collection of electrodes. The system also comprises a second traveling wave grid having a substrate, a plurality of closely spaced and parallel electrically conductive electrodes extending across the substrate, and a collection of buses providing electrical communication with the collection of electrodes on the substrate of the second traveling wave grid. The system further includes an effective amount of a fluid medium adapted to accommodate the agent undergoing concentration. The fluid medium is in contact with at least a portion of the electrodes on each of the two traveling wave grids. The system additionally includes at least one voltage controller which provides a multi-phase electrical signal to the collection of buses and electrodes of both the first and second traveling wave grids. The voltage controller is configured to apply the control signal to the first traveling wave grid and the second traveling wave grid such that the agent within the fluid medium at least partially travels or migrates across the first traveling wave grid in a direction generally perpendicular to the direction of the electrodes of that first grid. Then the agent further migrates through the fluid medium at least partially across the second traveling wave grid in a direction generally perpendicular to the direction of the second collection of electrodes disposed on the second traveling wave grid. By use of this system and preferably in this manner, a bio-agent or collection of bio-agents, or collection of particles, can be directed or focused into a relatively highly concentrated region.

Figure 7:
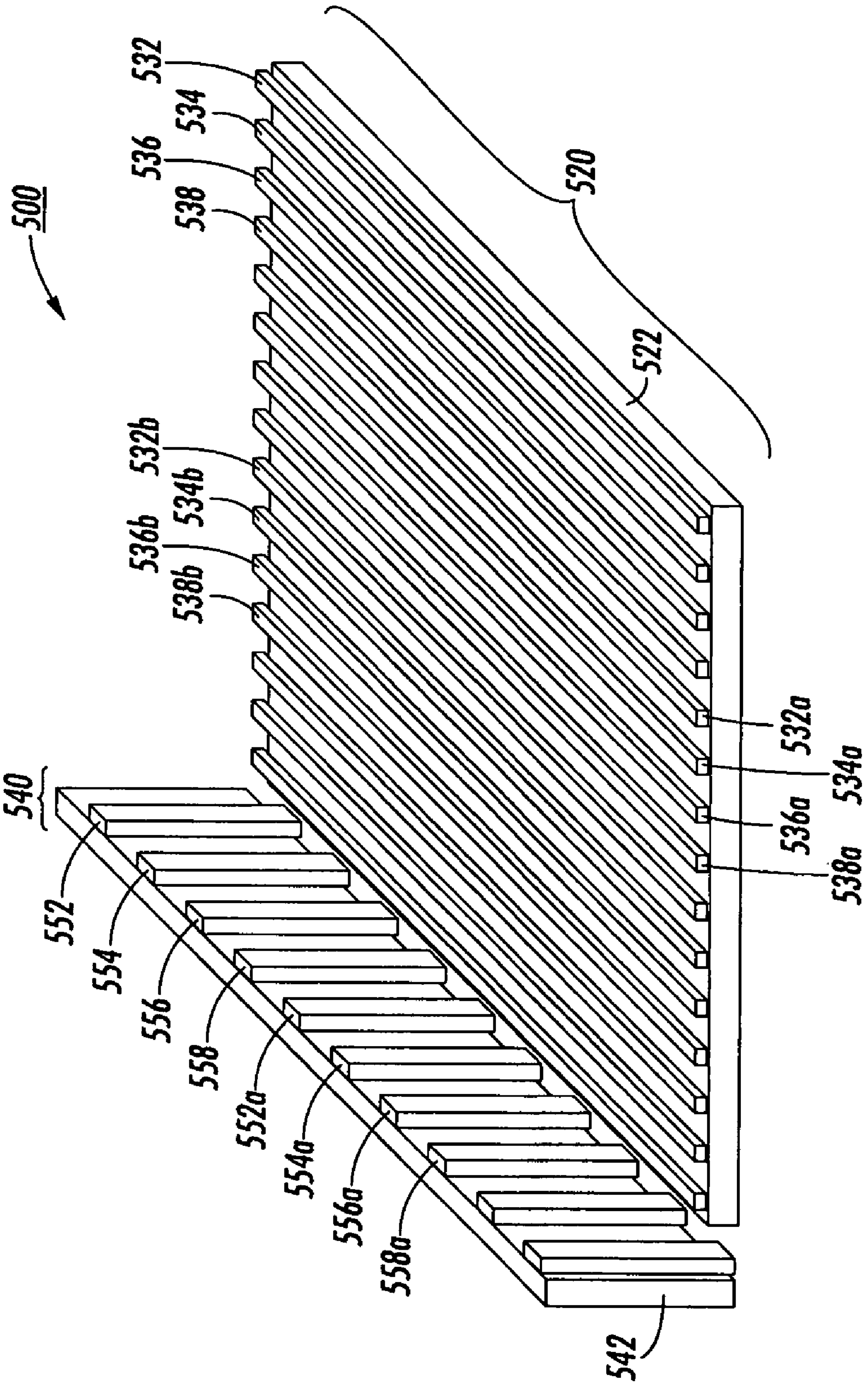
FIG. 7 is a schematic illustration of a preferred system of traveling wave grids.

Referring to FIG. 7, a traveling wave grid system 500 is illustrated. The system 500 comprises a first traveling wave grid 520 including a substrate 522 and a plurality of electrodes 532, 534, 536, and 538; 532*a*, 534*a*, 536*a*, and 538*a*; and 532*b*, 534*b*, 536*b*, and 538*b*. The system 500 also comprises a second traveling wave grid 540 including a substrate 542 and a plurality of electrodes 552, 554, 556, and 558; and 552*a*, 554*a*, 556*a*, and 558*a*. The grids 520 and 540 are preferably arranged at an angle with respect to each other. Preferably, this angle is in the range of 10° to 170°, 80° to 100°, and most preferably 90°. In this configuration all charged particles that are within the reach of the electric field generated from grid 520 are moved to the wall of grid 540. That is, particles suspended above the grid 520 are transported toward the grid 540, which in FIG. 7, is towards the left side of the grid 520. The grid 540 moves the particles along the corner or region of intersection of the grids 540 and 520, and concentrates the particles either in one region that is determined by the pulse sequence of the waveform or at one of the ends of grid 540, such as where a detector is placed. If diffusion of the particles is sufficiently suppressed (e.g. by using a high-viscosity transport medium), the particles will remain confined in a small area near the corner of the grids, and the second grid 540 can concentrate them into a single small region, i.e. typically less than 1 mm3.

Referring further to FIG. 7, in a preferred configuration, grid 520 concentrates the particles in line(s) parallel to its electrodes. The extent and manner of concentration depends on the pulse sequence and transport medium properties. Grid 540 concentrates the particles further into one or more individual regions of relatively high particle concentration. Because the effectiveness of a traveling wave grid decreases the further the particles are located from its electrodes, a biasing grid can provide a bias voltage to keep the particles in a thin layer just above the active grid and can also maintain a bias voltage to keep the particles from escaping from this layer while they are undergoing transport.

Figure 8:
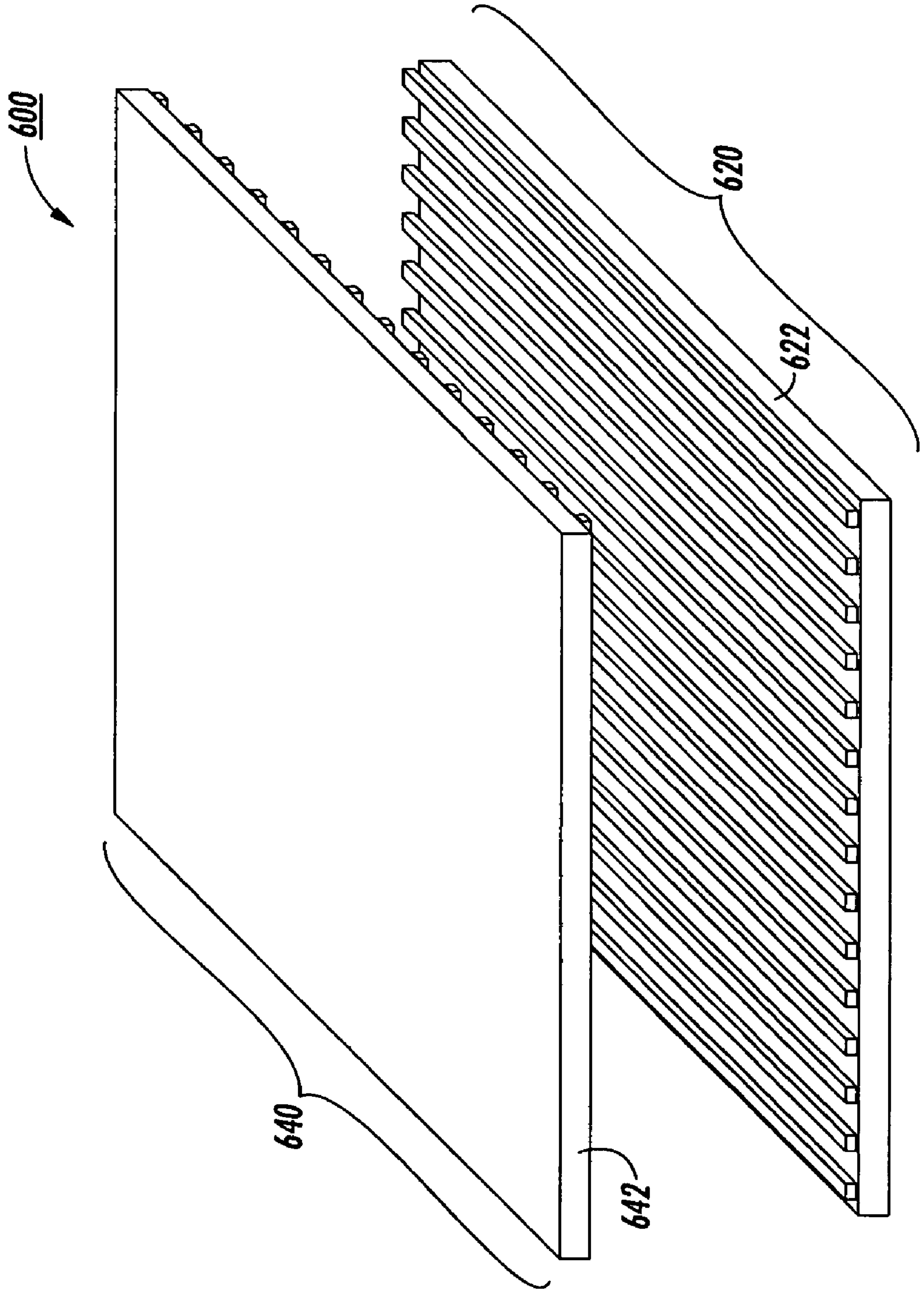
FIG. 8 is a schematic illustration of another preferred system of traveling wave grids.

Referring to FIG. 8, a system 600 of traveling wave grids is depicted. The system 600 comprises a first grid 620 having a plurality of electrodes disposed on a substrate 622. The system 600 also comprises a second grid 640 having a plurality of electrodes disposed on a substrate 642. During operation of the system 600, once the first grid 620 has concentrated the particles into line(s), a voltage potential may be applied between the two grids that will transfer the particles from a layer close to grid 620 to a layer close to grid 640. To keep the particles from spreading out, e.g. due to thermal diffusion, during the different steps of the concentration procedure, the medium between the two traveling wave grids should have a high (effective) viscosity such as is provided by a gel.

By use of a collection of traveling wave grids, the present work identified methods for transporting agents dispersed in a fluid medium in proximity to the grids, and more preferably, methods of concentrating these agents within certain regions of the medium. Using two traveling wave grids and one or more voltage controllers in selective electrical communication with the grids, a representative method for concentrating an agent is as follows. Once a fluid medium is placed in proximity to the two traveling wave grids, a control signal is sequentially applied to electrodes on the first grid. This manner of sequential activation of adjacent electrodes is as previously described herein. This operation induces movement of the agent in the fluid medium from one region to another region of the first grid. In the embodiment depicted in FIG. 7, such movement would be for example, from the right side of the grid 520 towards the left side of that grid. Preferably, this operation results in a region within the fluid medium having a relatively high concentration of agents.

After formation of the first region of relatively high concentration of agent, the control signal is sequentially applied to electrodes on the second traveling wave grid. This operation induces further movement of the agent in the fluid medium and preferably to a new location. In the embodiment of FIG. 7, the activation of the second grid 540 would cause a portion of the region extending along the left side of the first grid 520, to move toward the frontward portion of the grid 540. This causes a second region of high agent concentration to form, preferably adjacent a portion of the second grid 540. Most preferably, the concentration of agent in the second region is greater than the concentration of agent in the previously formed first region.

This method of concentrating one or more agents within a fluid medium is applicable to a wide array of configurations and arrangements of traveling wave grids. For instance, this method is suitable for the parallel arrangement of traveling wave grids depicted in FIG. 8.

Figure 9:
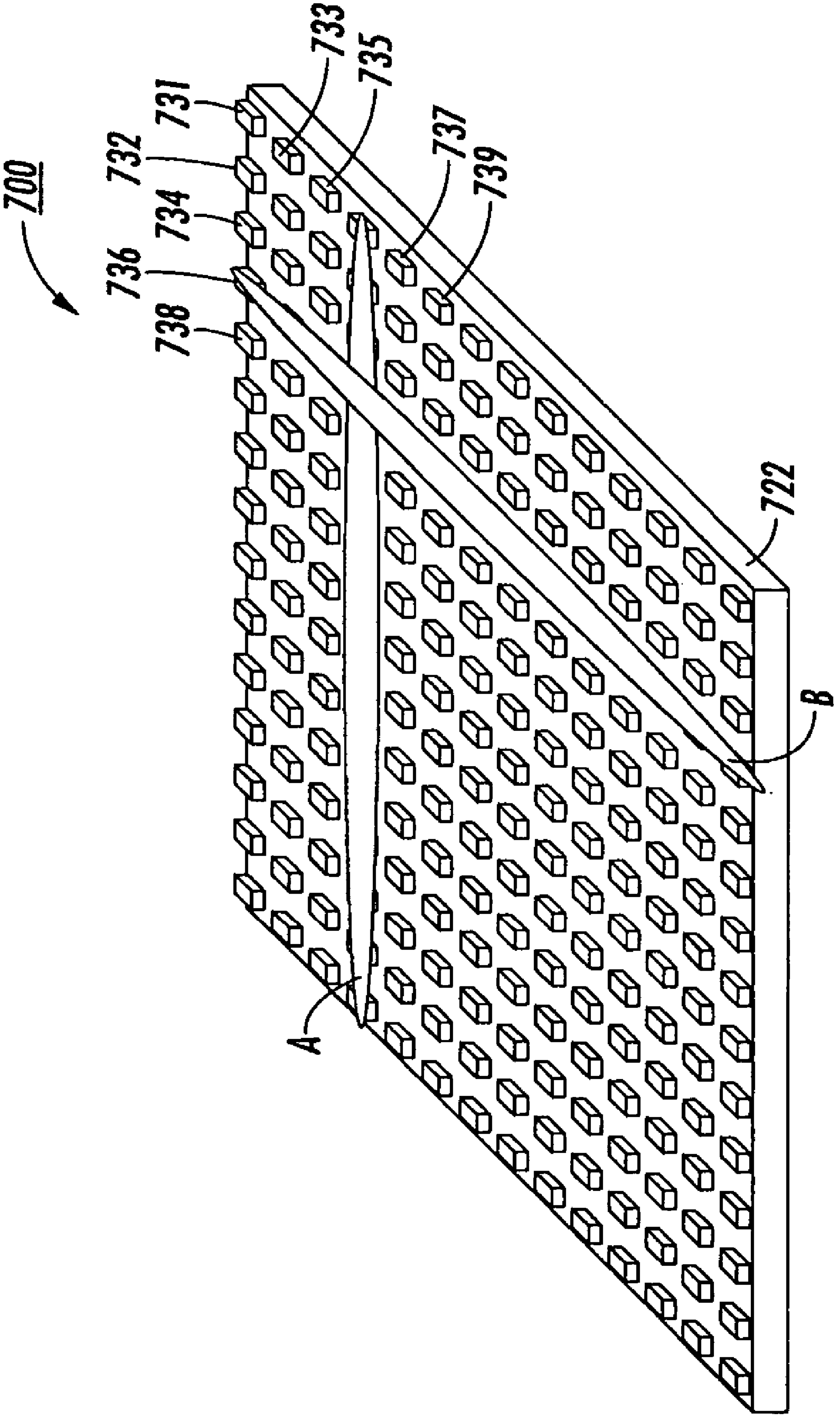
FIG. 9 is a schematic illustration of another preferred system of traveling wave grids.

In yet another embodiment of the present work, two or more grids maybe interspersed within each other. This is provided by a two-dimensional grid of "point" electrodes such as shown in FIG. 9. When coupled with one or more suitable voltage controllers, the resulting system is referred to herein as a selectively addressable traveling wave grid system. FIG. 9 illustrates a point electrode grid 700 comprising a plurality of point electrodes 731, 732, 733, 734, 735, 736, 737, 738, and 739, for example, which are all disposed on a substrate 722. By selectively controlling the application of an electrical signal to the point electrodes, the plurality or group of point electrodes may be operated to simulate a plurality of linear electrodes as previously described herein.

In this configuration shown in FIG. 9, charged particles can be moved in any direction based on the manner in which the individual electrodes are addressed. Alternatively, charged particles can be moved in any direction across or over the grid depending upon the manner in which traveling waves are applied to one or more of the point electrodes. In particular, one could emulate a grid composed of linear electrodes by driving or powering all point electrodes on rows perpendicular to the direction of motion with the same pulse phase. Thus, for example, regions with relatively high concentrations of bio-agents or particles, can be formed such as shown in FIG. 9 as regions A or B. After focusing the particles in lines or narrow regions, the traveling wave direction can be changed to concentrate the particles further into points or highly localized regions.

Specifically, a selectively addressable traveling wave grid system is provided which comprises a point electrode grid, a voltage controller, and a series of electrical contacts that provide electrical communication between each of the point electrodes and the voltage controller. As will be understood, each of the point electrodes may be placed in electrical communication with the controller such that the electrode may receive the control signal, or a phase thereof, independent of all or some of the other point electrodes. Thus, by appropriate selection of the point electrodes to receive the control signal, an extremely high number of patterns and electrode configurations maybe attained.

As shown in FIG. 9, a preferred arrangement of point electrodes on a substrate is an ordered array of linear rows and columns. Most preferably, the rows and columns of point electrodes are at right angles with respect to each other. The row and column arrangement enables a group of point electrodes which extend along a row, column, or portion thereof, to be concurrently activated and thus provide a similar function and effect as a single continuous linear electrode. Moreover, such a row and column arrangement of point electrodes also enables selected regions or groups of electrodes to be activated as desired. For example, a first row of point electrodes could be activated and receive a control signal. Next, a second row of point electrodes, proximate the previously activated first row, could be activated. Additional rows of point electrodes could subsequently be activated as desired to transport, concentrate, or focus agents dispersed along the grid. Upon a first set of row electrode activations, groups of point electrodes extending in columns on the grid are selectively activated. For instance, a first column of point electrodes could be activated and receive a control signal. Next, a second column of point electrodes, proximate the previously activated first column, could be activated. Additional columns of point electrodes could subsequently be activated as desired to transport, concentrate, or focus agents dispersed along the grid.

In another aspect of the present discovery, one or more traveling waves could be implemented on concentric circles or rather, patterns of point electrodes that would resemble or simulate circles, that would move all particles to the center of these circles. The present work further includes forming and moving bio-agents or particles through, and into, a wide range of shapes and patterns using a traveling wave grid comprising a plurality of point electrodes.

Using the point electrode grid described herein, the present work provides various methods for concentrating an agent dispersed within a fluid medium. The methods utilize systems having a point electrode grid including a substrate and a collection of individually addressable, electrically conductive point electrodes disposed on the substrate, a voltage controller providing a multi-phase control signal, and a collection of electrical contacts that provide electrical communication between the point electrode grid and the voltage controller. The methods generally involve the following steps. First, the fluid medium containing the agent to be concentrated is provided in relative close proximity to the point electrode grid. Next, a control signal, or portion thereof, is applied to a first portion of the collection of point electrodes which are disposed in a first row on the substrate. Next, the control signal is applied to a second portion of the collection of point electrodes that are disposed in a second row on the substrate. Preferably, the second row is adjacent or most preferably immediately adjacent to the first row. A region is formed in the fluid medium having a relatively high concentration of the agent. Preferably, the method is continued as follows. The control signal is applied to a third portion of the collection of point electrodes that are disposed in a first column on the substrate. And then, the control signal is applied to a fourth portion of the collection of point electrodes which are disposed in a second column on the substrate. As before, the second column is preferably adjacent and most preferably immediately adjacent to the first column of point electrodes. A second region is formed in the fluid medium having a relatively high concentration of the agent. As previously described herein, the arrangement of rows and columns are preferably at right angles to one another. Generally, the concentration of the agent in the second region which is formed is greater than the concentration of the agent in the first or initial region formed. And, the concentration of agent in both of these regions is generally greater than the initial concentration of agent dispersed within the fluid medium.

The present investigation provides a variety of strategies and methodologies for moving and selectively transporting bio-agents and particles. For example, referring to the previously described traveling wave grid systems, if the sample volume above a first grid such as grid 520, 620 extends beyond the reach of the grid, a bias voltage may be applied to urge the charged particles into or toward the active layer of the grid. This operation can occur outside the grid area, if it is desired to feed the particles continuously from one side into the grid. After concentrating all particles into line(s) or regions, either above the grid or at one end of the grid, particles may be transported to a second grid, such as grid 540, 640. Such a transfer may be performed using a bias electric field, if necessary. The transport direction of the second grid in most applications will be primarily perpendicular to that of the first. Next, the particles are concentrated along the lines into highly localized regions, either above the grid or at one end of the grid. In the case of the system 700 utilizing the point electrodes, concentration into highly localized regions can be achieved in one step with the appropriate traveling wave pattern. The appropriate traveling wave pattern can be comprised of a linear combination of the traveling wave patterns supplied by two individual standard grids.

In another aspect, the present discovery provides a system comprising a filter and one or more traveling wave grids to concentrate a wide array of particles, and preferably micron-sized particles, that are suspended in a liquid into a reduced volume to meet the limit of detectability (LOD) of a detector.

The preferred systems of the present discovery use a filter that selectively holds back or retains particles above a certain size range. Filters that purify or otherwise clean water from bacteria and viruses are widely available in different sizes and throughput rates. Although gravity flow designs are slow, i.e. tens of gallons per day, such filters do not need any electric power. Pump flow devices are substantially faster and can treat gallons per minute. These devices typically use a ceramic filter with a maximum pore size of 0.5 to 1 μm. Other nano-porous materials such as those made from aerogels, by packing non-ceramic nano particles, or by etching SiO2 wafers using electron-beam lithography, may also be used in the systems described herein.

Figure 10:
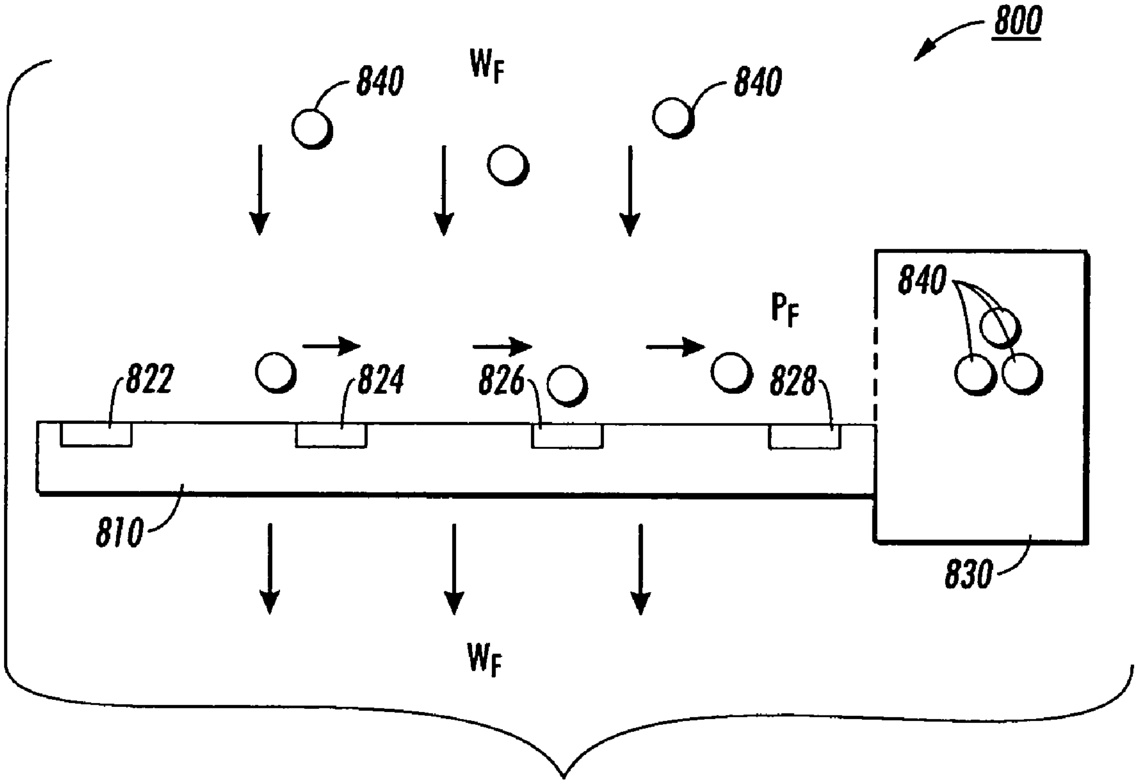
FIG. 10 is a schematic of a preferred filtering and detection system.

In order to achieve sufficiently high throughput, i.e. several gallons in a few minutes, it is generally necessary to provide a large filter surface. To further concentrate the bio-agents or particles, the systems described herein utilize traveling wave grids that are embedded or otherwise incorporated into the filter surface to concentrate the particles captured by the filter so they can be detected with appropriate sensors. Such a preferred system is depicted in FIG. 10. Furthermore, by combining several traveling wave grids, a two-dimensional distribution of bio-agents may be concentrated into a small volume or highly localized region at the detection zone.

Specifically, referring to FIG. 10, a system 800 is shown that comprises a sieve 810 or other filtering element that is disposed in close proximity with, or integrally formed with, a traveling wave grid having electrodes 822, 824, 826, and 828. The assembly of the sieve 810 and the traveling wave grid is in communication with an appropriate detector 830. During operation, a flow of liquid such as water flow WF is directed to the system of sieve and traveling wave grid such that the water passes through the sieve but particles in the water, such as particles 840, are trapped on the inlet side of the sieve. Upon operation of the traveling wave grid, the particles 840 are selectively transported to the detector 830. The transport or flow of trapped or retained particles is shown by Pf in FIG. 10. It will be appreciated that, as previously described, one or more additional traveling wave grids can be used to further tailor the resulting regions of high particle concentration.

Figure 11:
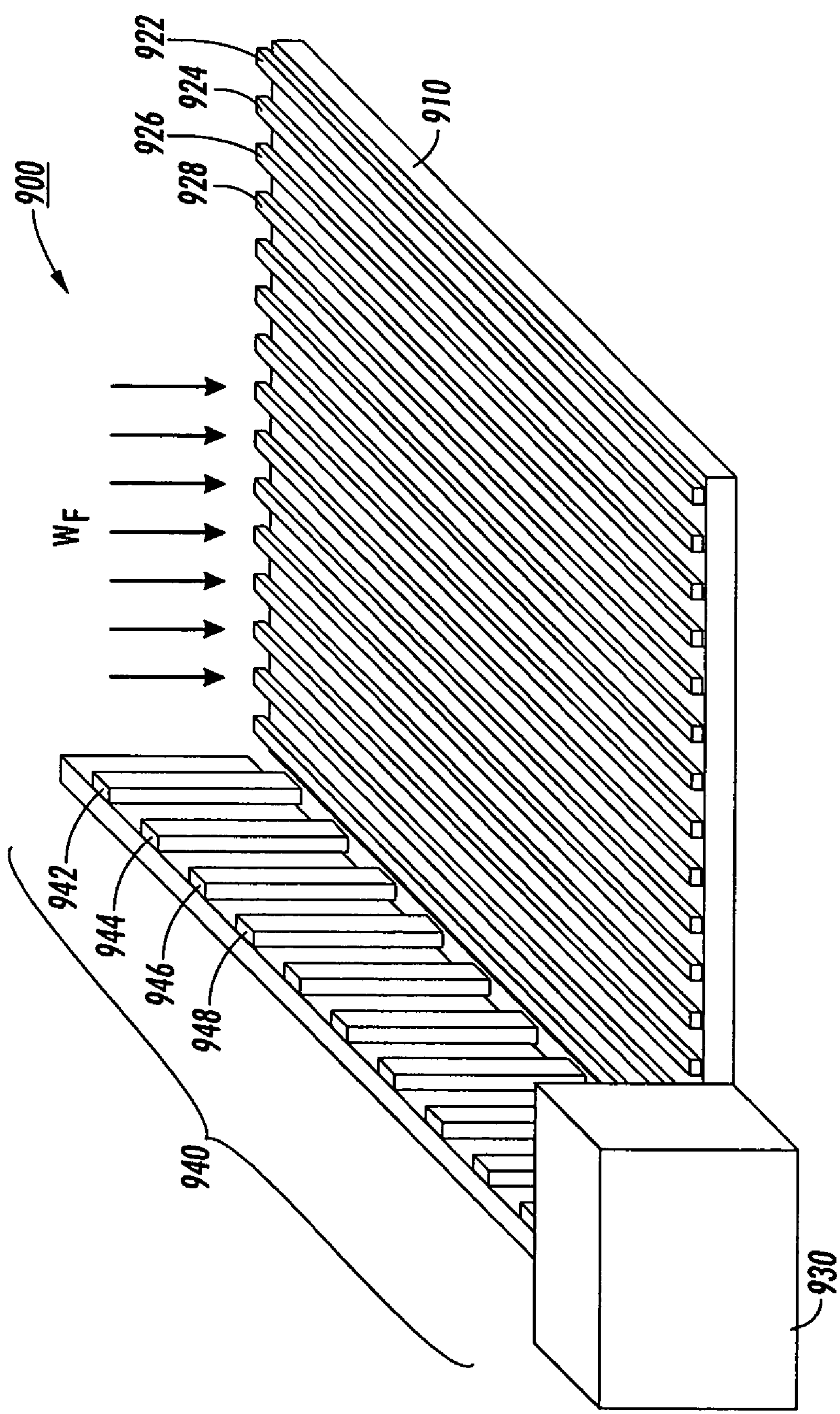
FIG. 11 is a schematic of another preferred filtering and detection system.

FIG. 11 illustrates another preferred embodiment system 900 in accordance with the present discovery. System 900 includes a sieve 910 having a first traveling wave grid incorporated therein with a plurality of electrodes such as 922, 924, 926, and 928. The system 900 also includes a bio-agent or particle detector 930, and a second traveling wave grid 940 having a plurality of electrodes such as 942, 944, 946, and 948. The second grid 940 is preferably disposed in-line or proximate the inlet port of the detector 930. Furthermore, the second grid 940 is preferably oriented at right angles with the first grid. During operation, a flow of liquid such as water, shown in FIG. 11 as WF , is directed toward the sieve 910 and traveling wave grid. Preferably, the contaminated water flows from the top to the bottom through the filter 910. Particles having a size larger than the pass-through size limit of the filter are held back and retained along the top of the filter surface. Upon operation of the traveling wave grid, i.e. electrodes 922, 924, 926, and 928, and the other electrodes disposed within the sieve 910, the trapped particles are moved along the top surface of the sieve in a direction parallel to the sieve surface. As the particles move from right to left in the diagram of FIG. 11, they collect in a region proximate the second grid 940. Upon operation of the second grid 940, the particles are then moved toward the detector 930 and specifically, into the inlet opening of that device.

Most colloidal particles develop a distinct charge when in solution and are therefore susceptible to the electric forces exerted on them from a traveling wave grid. In addition, since bacteria and viruses are easily polarizable, it is also possible to use dielectric forces to move or transport them with the traveling wave grids. Modes of operation can be continuous, i.e. a constant flow of water is maintained through the sieve, while moving all captured particles to the detector or discontinuous. In the continuous mode, care should be taken such that the flow rate is not too high to cause the particles to be pressed too firmly onto the sieving surface and thereby prevent their transport by the traveling wave grid.

In another mode of operation, i.e. the discontinuous mode, there exists a period with high flow through the sieve followed by a period of minimal or low flow where all the captured particles are moved to the detector using the traveling wave. To keep the particles close to the traveling wave grid, however, it would still be preferred for some liquid flow through the sieve.

In both modes of operation, the top surface of the sieve might need a specific surface treatment to prevent the bacteria and other agents from becoming immobilized on the surface. Since the surface of most bacteria is covered with "hairs" of poly-sugars, a similar monolayer of poly-sugars on the top surface of the sieve may be used to prevent the adhesion of bacteria through entropic repulsion, at least for short time scales such as on the order of seconds to minutes.

A wide array of bio-agents and particles may be selectively transported and concentrated into designated regions in accordance with the present subject matter. Table 1, set forth below, lists several representative bio-agents to which the present discovery is directed.

TABLE 1

Typical Bio-Agents and Their Dimensions

| | Size | Charge | Description |
|---|---|---|---|
| Bacteria | | | |
| Anthrax spore | 1–5 um | | |
| *E. coli* | 2 um | | |
| *Staphylococcus* | 2 um | | A category of bacteria that can cause boils, blood poisoning, and other serious infections |
| Virus | | | |
| Ebola virus | 200 nm | | An extremely contagious filovirus causing an acute, highly fatal hemorrhagic fever and spread through contact with bodily fluids or secretions of infected persons and by airborne particles. |
| Rhino virus | 20 nm | | Any of a genus (Rhinovirus) of picornaviruses that are related to the enteroviruses and are associated with upper respiratory tract disorders (as the common cold) |
| Toxin | 1–10 nm | | A poisonous substance, especially a protein, that is |

TABLE 1-continued

Typical Bio-Agents and Their Dimensions

| | Size | Charge | Description |
| --- | --- | --- | --- |
| | | | produced by living cells or organisms and is capable of causing disease when introduced into the body tissues but is often also capable of inducing neutralizing antibodies or antitoxins |
| Oocyte | | | |
| mammal | 100 um | | Oocyte: A cell from which an egg or ovum develops by meiosis; a female gametocyte |
| insect | 1000 um | | |
| frog/fish | 1–2 um | | |
| *Toxocara* parasite | 75–90 um | | *Toxocara* species are commonly found in wild and domestic animals. The eggs are identified by their thick corrugated shell, size and shape. *Neoascaris vitulorum*, in cattle (egg size 75 um × 90 um) |

The previously noted detection and filtering systems may be used in a variety of methods. For instance, the method for detecting agents in a flowing fluid medium using a system having a filter element adapted to collect agents dispersed in a fluid medium, a traveling wave grid having a plurality of electrically conductive electrodes disposed on the filter element, a voltage controller adapted to provide a multi-phase control signal to the collection of electrodes, and a detector adapted to detect agents in the fluid medium, may be used in a method as follows. First, the previously noted grid and filter are positioned in the flowing fluid medium such that the traveling wave grid is upstream of the filter element. Agents dispersed in the flowing fluid medium are collected on the filter element. Specifically, it will be understood that the agents having a size greater than the pass-through limit of the filter are those that are collected. The traveling wave grid is operated by selectively applying the control signal from the voltage controller to portions of the collection of electrodes in order to induce movement of the collected agents along the face of the filter element. Preferably, all of the collected agents are moved toward one dedicated region along the traveling wave grid and/or filter element. This dedicated region is preferably proximate or adjacent the detector and most preferably near the inlet of the detector. Thus, the traveling wave grid can induce movement of the collected agents from the filter element to the inlet of the detector. The now relatively high concentration of collected agents can be detected or otherwise analyzed by the detector or other instrument.

The invention has been described with reference to the preferred embodiments. Obviously, modifications and alterations will occur to others upon reading and understanding the preceeding detailed description. It is intended that the invention be construed as including all such modifications and alterations insofar as they come within the scope of the appended claims or the equivalents thereof.

What is claimed is:

1. A system for selectively concentrating an agent within a fluid medium, said system comprising:

a first traveling wave grid having (i) a first substrate, (ii) a first plurality of closely spaced and parallel electrically conductive electrodes extending across said first substrate, and (iii) a first plurality of buses providing electrical communication with said first plurality of electrodes;

a second traveling wave grid having (i) a second substrate, (ii) a second plurality of closely spaced and parallel electrically conductive electrodes extending across said second substrate, and (iii) a second plurality of buses providing electrical communication with said second plurality of electrodes, wherein the plane of the second grid is oriented at an angle of from 10° to 170° with respect to the first grid;

an effective amount of a fluid medium adapted to accommodate said agent undergoing migration therein, said fluid medium in contact with at least a portion of said first plurality of electrodes and at least a portion of said second plurality of electrodes;

at least one voltage controller providing a multi-phase electrical control signal to said first plurality of buses, said first plurality of electrodes, said second plurality of buses, and said second plurality of electrodes, wherein said voltage controller is configured to apply said control signal to said first traveling wave grid and said second traveling wave grid such that said agent migrates through said fluid medium at least partially across said first traveling wave grid in a direction generally perpendicular to the direction of said first plurality of electrodes, and then further migrates through said fluid medium at least partially across said second traveling wave grid in a direction generally perpendicular to the direction of said second plurality of electrodes.

2. The system of claim 1 wherein said first traveling wave grid is oriented at an angle of approximately 90° from said second traveling wave grid.

3. The system of claim 1 further comprising:

a planar conductor providing a voltage potential with respect to at least one of said first traveling wave grid and said second traveling wave grid to thereby provide a bias field.

4. A method for concentrating an agent dispersed within a fluid medium by use of a system of traveling wave grids, said system including (i) a first traveling wave grid having a substrate, a plurality of electrodes, and buses providing electrical communication with said electrodes, (ii) a second traveling wave grid having a substrate, a plurality of electrodes, and buses providing electrical communication with said electrodes of said second grid, where in the plane of the second grid is oriented at an angle of from 10° to 170° with respect to the first grid, and (iii) a voltage controller providing a control signal to said electrodes of said first and second traveling wave grids, said method comprising;

providing said fluid medium containing said agent in proximity to said first and said second traveling wave grids;

sequentially applying said control signal to said plurality of electrodes of said first traveling wave grid to induce movement of said agent in said fluid medium to form a first region in said medium of high concentration of agent;

sequentially applying said control signal to said plurality of electrodes of said second traveling wave grid to induce further movement of said agent in said fluid medium to thereby form a second region in said medium of high concentration of agent.

5. The method of claim 4 wherein the concentration of agent in said second region is greater than the concentration of agent in said first region.

6. The method of claim 4 wherein the concentration of agent in both said first region and said second region is greater than the initial concentration of agent in said medium.

7. A system for detecting agents in a flowing fluid medium, said system comprising:

a filter element adapted to collect agents dispersed in a fluid medium having a size greater than the pass-through size limit of said filter element;

a traveling wave grid having a plurality of electrically conductive electrodes disposed on said filter element;

a voltage controller adapted to provide a multi-phase control signal to said plurality of electrodes and transport collected agents on said filter element; and a detector adapted to detect said agents in said fluid medium, said detector disposed in proximity to a region of said traveling wave grid;

wherein upon operation of the system, collected agents on said filter element are transported to said detector.

8. The system of claim 7 further comprising:

a second traveling wave grid having a substrate and a plurality of electrically conductive electrodes disposed on said substrate, said second grid positioned proximate to said traveling wave grid disposed on said filter element.

9. The system of claim 7 further comprising:

a planar conductor providing a voltage potential with respect to said traveling wave grid to thereby provide a bias field.

10. A method for detecting agents in a flowing fluid medium using a system having (i) a filter element adapted to collect agents dispersed in a fluid medium having a size greater than the pass-through size limit of said filter element, (ii) a traveling wave grid having a plurality of electrically conductive electrodes disposed on said filter element, (iii) a voltage controller adapted to provide a multi-phase control signal to said plurality of electrodes, and (iv) a detector adapted to detect said agents in said fluid medium, said detector disposed proximate to a region of said traveling wave grid, said method comprising:

positioning said filter element and said traveling wave grid of said system in said flowing fluid medium such that said traveling wave grid is upstream of said filter element;

collecting said agents having a size greater than the pass-through size limit of said filter element, along said filter element;

activating said traveling wave grid by selectively applying said control signal from said voltage controller to portions of said plurality of electrodes whereby said agents collected on said filter element are moved to said detector;

detecting said agents moved from said filter element by said traveling wave grid and said controller.

11. The method of claim 10 wherein said flowing fluid medium is water.

* * * * *

UNITED STATES PATENT AND TRADEMARK OFFICE

CERTIFICATE OF CORRECTION

PATENT NO. : 7,163,611 B2
APPLICATION NO. : 10/727289
DATED : January 16, 2007
INVENTOR(S) : Armin R. Volkel et al.

It is certified that error appears in the above-identified patent and that said Letters Patent is hereby corrected as shown below:

On page 13 of the patent, at Column 1, after the Title and before the heading "TECHNICAL FIELD", insert the following:

This invention was made with Government support under DAAD19-03-C-0116 awarded by the U.S. Army. The Government has certain rights in this invention.

Signed and Sealed this

Third Day of April, 2007

JON W. DUDAS
*Director of the United States Patent and Trademark Office*